(12) United States Patent
Dykes et al.

(10) Patent No.: US 7,357,811 B2
(45) Date of Patent: Apr. 15, 2008

(54) INTEGRATED PROCEDURE LIGHT FOR INFANT CARE APPARATUS

(75) Inventors: Christopher A. Dykes, Columbia, MD (US); Michael H. Mackin, Ellicott City, MD (US)

(73) Assignee: General Electric Company, Schenectady, NY (US)

( * ) Notice: Subject to any disclaimer, the term of this patent is extended or adjusted under 35 U.S.C. 154(b) by 390 days.

(21) Appl. No.: 10/691,048

(22) Filed: Oct. 22, 2003

(65) Prior Publication Data
US 2005/0090879 A1   Apr. 28, 2005

(51) Int. Cl.
*A61N 5/00* (2006.01)
*A61G 11/00* (2006.01)

(52) U.S. Cl. .......................................... 607/90; 600/22

(58) Field of Classification Search .................. 607/88, 607/90–91; 600/22; 362/268–269
See application file for complete search history.

(56) References Cited

U.S. PATENT DOCUMENTS

| | | | |
|---|---|---|---|
| 2,607,881 A | | 8/1952 | Anderson |
| 4,101,957 A | * | 7/1978 | Chang ........................ 362/268 |
| 4,161,172 A | * | 7/1979 | Pickering ..................... 600/22 |
| 4,646,214 A | * | 2/1987 | Mendleski ................... 362/294 |
| 4,809,677 A | | 3/1989 | Mackin |
| 4,882,667 A | * | 11/1989 | Skegin ........................ 362/373 |
| 5,068,767 A | | 11/1991 | Koyama |
| 5,347,431 A | | 9/1994 | Blackwell et al. |
| 5,383,105 A | | 1/1995 | Agut et al. |
| 5,820,253 A | * | 10/1998 | Scholz ........................ 362/267 |
| 5,830,123 A | * | 11/1998 | Franz et al. ................... 600/22 |
| 5,915,072 A | * | 6/1999 | Campbell et al. ........... 392/418 |
| 6,402,681 B1 | | 6/2002 | McDonough et al. |
| 6,413,205 B1 | | 7/2002 | Finny |

FOREIGN PATENT DOCUMENTS

| | | |
|---|---|---|
| DE | 94 18 339.2 | 1/1995 |
| EP | 1 247 511 | 10/2002 |
| FR | 1 604 466 | 11/1971 |
| WO | WO 02/28341 | 4/2002 |
| WO | WO 03/072995 | 9/2003 |

OTHER PUBLICATIONS

Data Sheet from First Gulf International for Intensive Care Infant Warmer, copyright 2001-2004.*

* cited by examiner

*Primary Examiner*—Roy D. Gibson
(74) *Attorney, Agent, or Firm*—Roger M. Rathbun

(57) ABSTRACT

An infant warming apparatus for supporting an infant upon an infant platform. The apparatus has a procedure light that is recessed into the normal horizontal overhead housing of the apparatus and thus integrated into the infant apparatus. The procedure light is conveniently located above and centrally positioned with respect to the infant so as to direct the light toward the infant. The mounting provides omnidirectional movement of the procedure light and the movement can be easily controlled by means of a control handle that extends downwardly with a distal end readily accessible to the caregiver. At or proximate to the distal end there is an electrical controller to enable the caregiver to change the intensity of the light beam. The light beam can also be easily focused so as to allow the caregiver to direct the desired beam of light onto the area of interest of the infant.

20 Claims, 4 Drawing Sheets

INTEGRATED PROCEDURE LIGHT FOR INFANT CARE APPARATUS

BACKGROUND

The present invention relates to an infant warming apparatus and, more particularly, to an examination/procedure light that is integrated into an infant care apparatus.

In the care of newborn infants, there is an infant warmer apparatus that is used to provide warming of the infant and to supply the necessary heat to maintain the infant at a predetermined temperature. The infant warmer basically comprises a planar surface on which the infant is positioned and which planar surface normal includes side guards to keep the infant safely within the confines of the apparatus.

Infant warmers normally also have a overhead radiant heater that is located above the infant and which thus radiates energy in the infrared spectrum to impinge upon the infant to maintain the infant at the desired temperature. With infant warmers, since the infant is otherwise totally exposed to the surroundings, there is almost unlimited access to the infant by the attending personnel to perform various procedures on that infant. A typical infant warmer is shown and described in U.S. Pat. No. 5,474,517 of Falk et al as prior art to that patent.

Since there is such wide open access to the infant, the infant warmer is normally used where there is some intervention or procedure to be carried out on the infant while resting on the planar surface. Since some, if not all, of such procedures are delicate, it is normally necessary to have some source of illumination of the infant so that the attending personnel can have sufficient light to view the infant as a whole, or to concentrate the light on a localized region of the infant in carrying out the procedure.

Accordingly, with infant warmers, there is generally a procedure light that is separately and independently provided with an infant warmer and which is either set up to be a free standing light or is affixed to the infant warmer in some manner as an add-on to the infant warmer. Such lights are also mounted so as to be movable so that the beam of light can be moved to the particular location on the infant where the light is needed.

Alternatively, there is disclosed in U.S. Pat. No. 6,413,205 of Finny, a light that is mounted in the overhead housing of an infant warmer, however, the light of the Finny patent is a fixed light having no apparent means of moving the light beam to a specific location and also, there is no means disclosed where the light beam of the Finny patent can be focused between a broad beam and a smaller, focused beam.

Accordingly, it would be advantageous to have a integrated mounting for the procedure light so that the procedure light can be centrally located and can be built into the infant warmer and which may also be manually movable, omni-directionally, by the user as well as being focusable so that the user can broaden or narrow the beam of light.

SUMMARY OF THE INVENTION

Accordingly, the present invention relates to an infant warmer that has a procedure light that is integrated into the overhead housing that is normally a part of the infant warmer as manufactured. Therefore, rather than providing an add-on procedure light that is retrofitted alongside an existing overhead housing of an infant warmer, or a fixed built in light, use is actually made of that already present overhead housing of the infant apparatus by actually using that upper housing as a base or supporting structure for the integration of the procedure light.

The procedure light is thus conveniently located in a central location of the infant warmer and has a control handle that extends downwardly so as to be located in easy access by the personnel so that the light can be manually moved to direct the beam onto the desired position. Thus, by a omni-directional movable mounting system, such as a gimbaled mounting mechanism, or by means of overlapping spherical housings, the procedure light can be manually moved omni-directionally, that is, in any direction, by the caregiver to direct the beam to the particular area of the infant when illumination is desired.

The procedure light can also have a focusing means whereby the procedure light can cast a broad beam or a narrow beam to focus on a particular area of the infant. Also, the procedure light can have a variable iris that can be used to widen or reduce the width of the beam emitted from the procedure light and, additionally, the procedure light can have an electrical controller located on the chassis of the infant warmer, or actually incorporated into the control handle of the procedure light, such that the procedure light can have its intensity varied in accordance with the needs of the caregiver.

As additional features or alternative embodiments, the procedure light may be adapted to act as a phototherapy light for the alleviation of billirubinemia by utilizing a bulb of a particular wavelength or by a bulb having a filter that provides the desired wavelength. There may also be used, a color filter added to the apparatus such that the user can utilize light of a particular desired color to shine upon the infant.

These and other features and advantages of the present invention will become more readily apparent during the following detailed description taken in conjunction with the drawings herein.

DETAILED DESCRIPTION OF THE INVENTION

Figure 1:
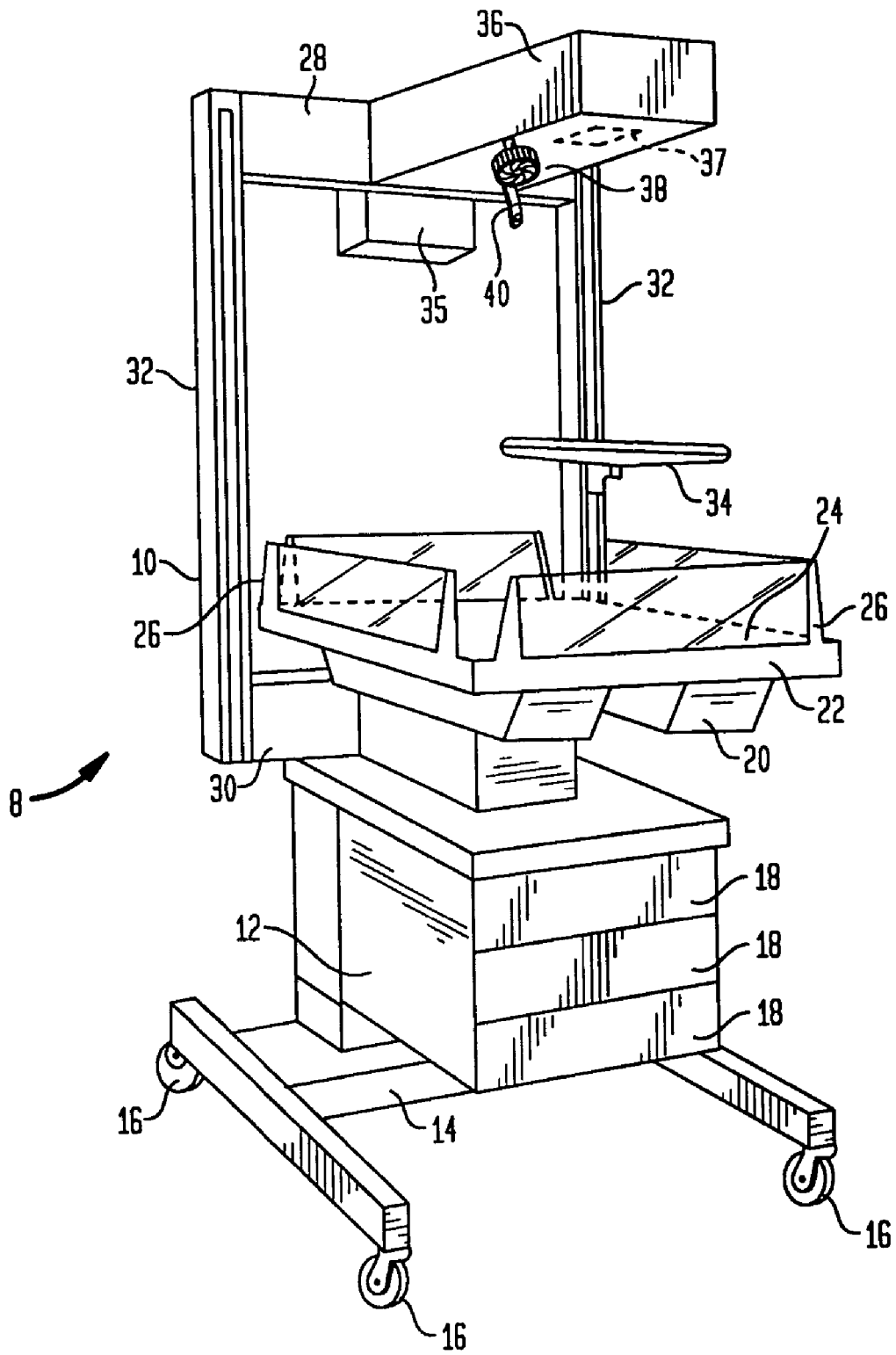
FIG. 1 of a perspective view of an infant warming apparatus having a procedure light integrated therein in accordance with the present invention.

Referring now to FIG. 1, there is shown a perspective view of an infant warmer 8 constructed in accordance with the present invention. As shown, the infant warmer 8 includes a frame 10 which provides a free standing unit for the infant warmer 8. The frame 10 is support upon a cabinet 12 which, in turn, is mounted upon a base 14 having wheels 16 so that the infant warmer 8 is easily movable. The cabinet 12 may also include one or more drawers 18 for containing items for attending to the infant.

An infant platform 20 is mounted atop of the cabinet 12 and on which is located an infant bed 22 which underlies and supports an infant positioned thereon. Infant platform 20 is the main support for the infant bed 22. The infant bed 22 has a generally planar upper surface 24 with appropriate cushioning material for comfort of the infant and further may be surrounded by guards 26, generally of a clear plastic material that contain the infant on the upper surface 24. Normally, the guards 26 are removable and/or releasable for complete access to the infant.

Frame 10 includes upper and lower cross members 28 and 30, respectively, joining a pair of vertical struts 32 and which vertical struts 32 may provide a means of support for other structural components such as a shelf 34.

Mounted on the upper cross member 28 may be a control module 35 that is conveniently positioned intermediate the vertical struts 32 and can include displays of various monitored parameters as well as include the various controls for operation of the functions of the infant warming apparatus 10. In addition, there is an overhead housing 36 mounted to the upper cross member 28 and which contains a radiant heater 37 that directs infrared energy toward an infant lying on the infant bed 22 in order to provide warmth to the infant.

As also can be seen in FIG. 1 there is a procedure light 38 that is recessed into and integrally mounted in the overhead housing 36 and which is constructed and affixed to the overhead housing 36 in accordance with the present invention and which has a control handle 40 extending downwardly from the procedure light 38 so as to be within the reach of the caregiver to manipulate the position of the procedure light 38 in a manner that will be later described.

Figure 2:
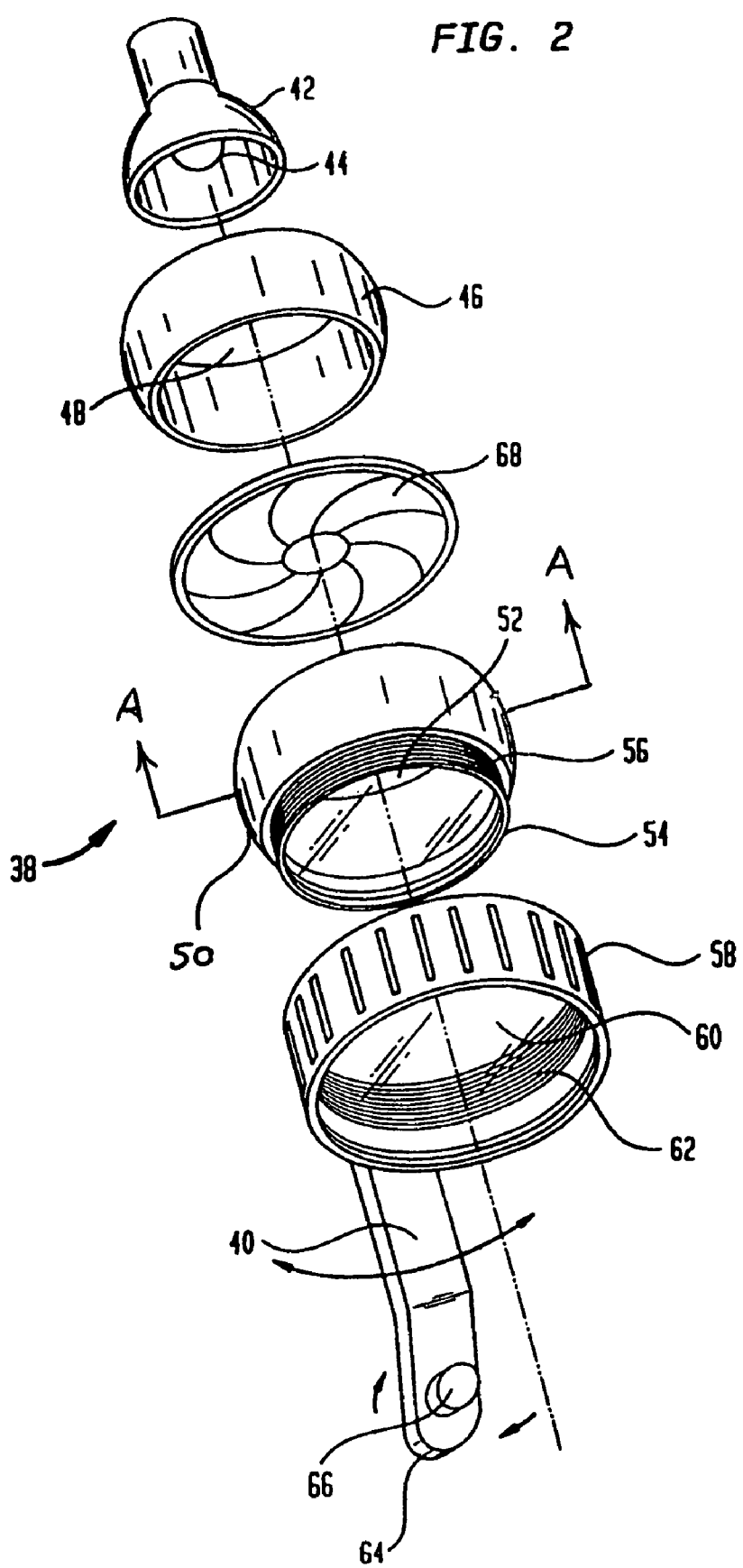
FIG. 2 is an exploded view of the procedure light of the present invention.

Turning now to FIG. 2 there is shown an exploded view of the procedure light 38 of the present invention and showing the individual components that can be used in the invention. In FIG. 2, therefore, there can be seen a light bulb enclosure 42 containing a light bulb 44 that is, of course, adapted to be connected to a source of electricity for operation thereof and the inner surface of the light bulb enclosure 42 is conventionally coated with a reflective material. In the preferred embodiment, the light bulb 44 and the light bulb enclosure 42 are both affixed to the overhead housing 36 (FIG. 1) so as to be in a fixed position with respect to the overhead housing 36.

As indicated, in an alternative embodiment, the bulb can be selected so as to have the desired wavelength that is particularly adapted to alleviate bilirubinemia or a bulb can be used in conjunction with a filter that produces the desired wavelength so that the built in procedure light 38 can be utilized for phototherapy for an infant. As a further alternative, there may be a filter added to the light bulb 44 or light bulb enclosure 42 so that a particular color of light can emanate from the procedure light as desired by the user.

An upper housing 46 is also positioned having an opening 48 that is coaxially aligned with the light bulb 44 and the light bulb enclosure 42. The shape of the upper housing 46 is preferably a truncated spherical configuration and the purpose of that particular shape will become apparent.

A lower housing 50 is also present and which is also, preferably, in the shape of a truncated sphere and which has a radius that is slightly larger than the radius of the spherical configuration of the upper housing 46. The lower housing 50 also has an opening 52 that is in alignment with the opening 48 of the upper housing 46 and, in the assembly of the procedure light 38, the lower housing 50 surrounds the upper housing 46 in a close interfitting relationship so that the lower housing 50 is affixed to the upper housing 46 but is free to move about that upper housing 46 in an omnidirectional manner, that is, the lower housing 50 can move with respect to the upper housing 46 in any direction and the movement is not, therefore, constrained to any finite or limited number of directions. A line having arrows A-A is also shown in FIG. 2 through the lower housing 50 to indicate those components that are recessed into the overhead housing 36 (FIG. 1) and are located in the direction of the arrows A.

Alternatively, other means of providing omni-directional movement of the procedure light 38 could be used in affixing the procedure light 38 to the overhead housing 36 such as a gimbaled arrangement.

As also can be seen, there is a cylindrical flange 54 that extends outwardly from the lower housing 50 and that circular flange 54 has external threads 56 formed thereon.

There is a lens holder 58 that retains a lens 60 and which has internal threads 62 formed therein such that the internal threads 62 are compatible and therefore mate with the external threads 56 formed on the cylindrical flange 54. The lens 60 can be a standard concave/convex lens and which can therefore focus the light beam emitted by the light bulb 44 and which passes through the opening 48, the opening 52 and then through the lens 60 to be directed toward the infant bed 22 (FIG. 1) on which an infant is located.

Accordingly, as is now apparent, the lens holder 58 can be rotated in order to move the lens holder 58 relative to the lower housing 50 so as to move the lens 60 toward and away from the light bulb 44 such that the rotation of the lens holder 58 focuses the light beam emanating from the procedure light 38 onto the infant bed 22 (FIG. 1) to be able to focus the beam of light as desired by the caregiver.

In FIG. 2, there can also be seen the control handle 40 that extends outwardly from the lens holder 58 to a distal end 64. At or proximate to that distal end 64, there is, in the preferred embodiment, an electrical controller 66 that is used to control the electrical power to the light bulb 44. That electrical controller 66 may be a simple on-off switch or may be a finer control of the power such as to provide a variable control of the power to the light bulb 44 to be able to vary the intensity of the beam of light from the light bulb 44 in accordance with the desire of the caregiver. Alternatively, of course, there may be a light controller located on the control module 35 (FIG. 1) or in some other convenient location for the caregiver.

As a further component of the present procedure light 38, and which may be optional, there can be a controllable iris 68 affixed to or affixable as an add on to the lens holder 58 so that the beam of light emitted from the procedure light 38 may be controlled as to its diameter, that is, the caregiver can narrow down the width of the beam of light to locate that beam upon an infant at a desired location thereon. Therefore, by a manual control of the controllable iris 68, the caregiver has an addition control over the beam of light in addition to the focusing feature that is provided by means of movement of the lens 60 with respect to the light bulb 44.

Figure 3:
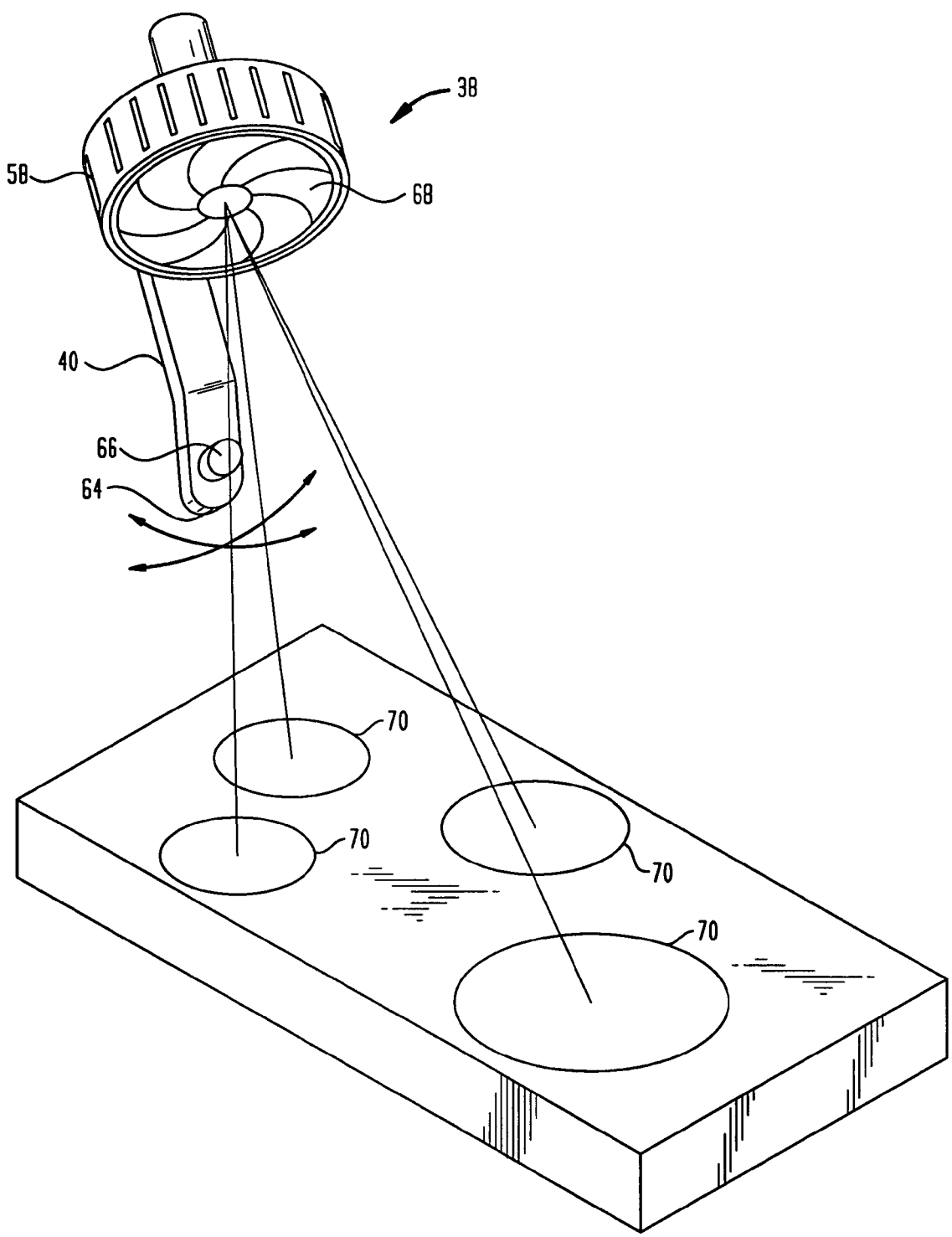
FIG. 3 is a schematic view of the procedure light of the present invention showing its use in providing light onto an infant platform.

Turning now to FIG. 3, there is shown a schematic view of the present procedure light 38 apart for the overhead housing 36 (FIG. 1) within which it is located and illustrating the versatility of the beam of light emitted therefrom. For example by a simple manual movement of the control handle 40 the beam of light emitted from the procedure light 38 can be moved to any of the positions 70 on the infant bed 22 (FIG. 1) and such that the omnidirectional movement of the procedure light 38 is movable to any of such positions 70 easily and directly.

In addition, as also can be seen in FIG. 3, the diameter of the light beam on the infant bed 22 may be focused in accordance with the operation of the lens 60 (FIG. 2) moving toward or away from the light bulb (FIG. 2) and the diameter of the beam of light that impinges upon the infant bed 22 can be widened or narrowed by the operation of the controllable iris 68. In any case, the direction, focus and diameter of the light beam is readily changed in accordance with the particular desire of the caregiver intent on having a focused illumination of a portion of the infant or more spread out to encompass the entire infant while the procedure light 38 itself is recessed into the normal overhead housing 36 (FIG. 1) of the infant warmer 8.

Figure 4A:
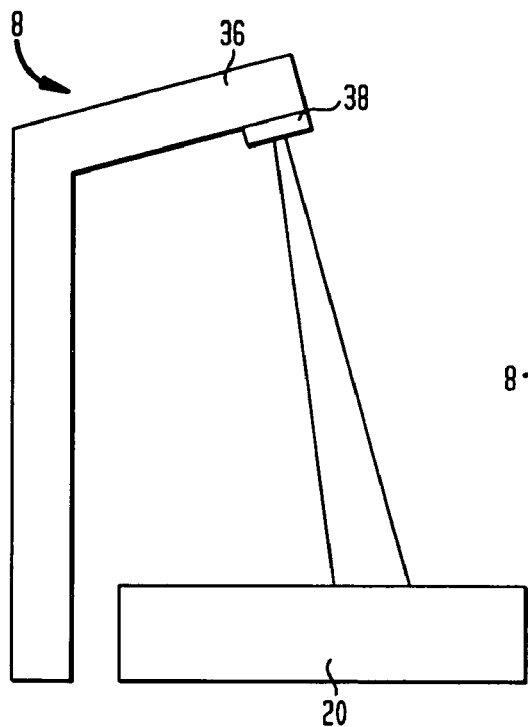
FIG. 4A and FIG. 4B are schematic views showing the further uses of the procedure light of the present invention.
Figure 4B:
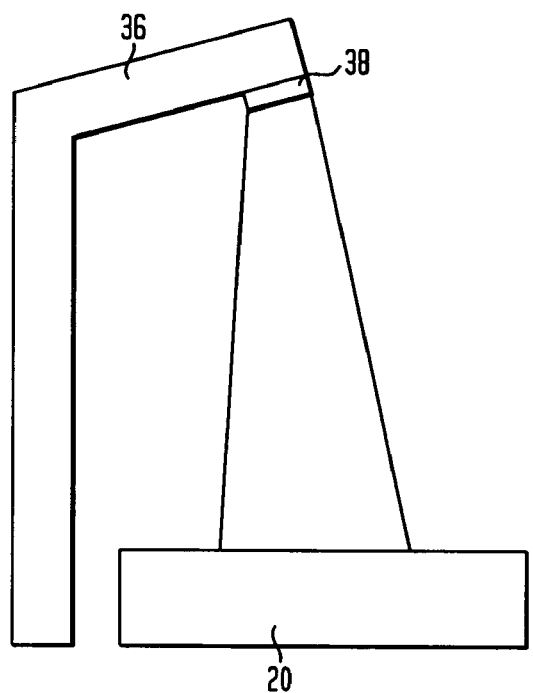

The focusing feature is shown in FIGS. 4A and 4B, taken along with FIGS. 1 and 2, where it can be seen that the procedure light 38 is recessed into the overhead housing 36 of the infant warmer 8 and by focusing the light beam by means of the threaded engagement between the lens holder 58 and the lower housing 50, the beam of light can be focused on to the infant platform 20 to the particular area of the infant where the light is desired, and as can be also seen, in FIG. 4A, the diameter of the beam of light can be in the form of a relatively small spot 72 and in FIG. 4B the beam of light can be in the form of a relatively large spot 74 and that diameter adjusted by the caregiver by the manipulation of the controllable iris 68.

Figure 5:
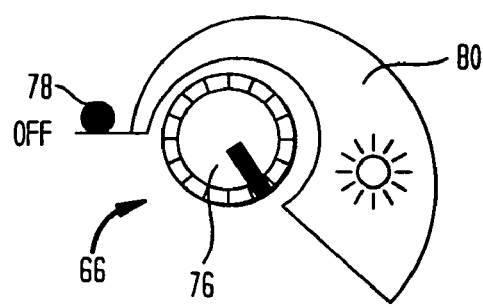
FIG. 5 is a schematic view of a controller that can be used with the present invention.

Finally, turning to FIG. 5, there is shown a schematic view of an electrical controller 66 that can be used with the present invention. In FIG. 5, there is a rotatable knob 76 that is affixed to the electrical controller itself and which may be a rheostat or solid state device that has an "off" position 78 and where the rotatable knob 76 can increase the power to the light bulb 44 (FIG. 2) as the rotatable knob 76 is rotated in accordance with the indicia 80 that may be provided on a face plate or decal proximate to the rotatable knob 76.

As such, the electrical controller 66 can, as indicated, be located, in the preferred embodiment, at the distal end 64 of the control handle 40 (FIG. 2) for the convenience of the caregiver in having the control in a convenient location, or, alternatively and more conventionally, the electrical controller 66 can be located on the control module 35 (FIG. 1) which is within the easy reach of the caregiver.

Those skilled in the art will readily recognize numerous adaptations and modifications which can be made to the infant care apparatus of the present invention which will result in an improved procedure light for an infant care apparatus, yet all of which will fall within the scope and spirit of the present invention as defined in the following claims. Accordingly, the invention is to be limited only by the following claims and their equivalents.

We claim:

1. An infant warming apparatus, said infant warming apparatus comprising a base having an infant platform on which an infant is adapted to be positioned, an overhead housing located in a fixed position above the infant platform, a procedure light having a light source, said procedure light being recessed within the overhead housing for omnidirectional movement with respect to the overhead housing and positioned so as to direct a beam of light from said light source toward the infant platform, a control handle extending downwardly from the procedure light so as to be accessible to a person to adjust the direction of the beam of light from said procedure light.

2. The infant warming apparatus as defined in claim 1 wherein said procedure light comprises an upper light housing and a lower light housing, the upper and lower light housings being shaped so as to conform closely and to interfit with each other, the upper light housing being fixed to the overhead housing and the lower light housing being movable with respect to the upper light housing so as to be adjustable to direct the beam of light toward different locations on said infant platform.

3. The infant warming apparatus as defined in claim 2 wherein the upper and lower light housings are both shaped in the form of truncated spheres, with the lower light housing substantially surrounding the upper light housing.

4. The infant warming apparatus as defined in claim 1 wherein the procedure light further includes a lens, and wherein the lens is manually movable with respect to the light source to focus the beam of light directed from the light source toward the infant platform.

5. The infant warming apparatus as defined in claim 4 wherein said lens is mounted to a lens holder and wherein said lens holder is affixed by a threaded engagement to said lower light housing and said lens holder is rotatable by the threaded engagement to move the lens with respect to the lower light housing.

6. The infant warming apparatus as defined in claim 5 wherein the lens holder has internal threads and the lower light housing has a flange extending therefrom having external threads to form the threaded engagement therebetween.

7. The infant warming apparatus as defined in claim 1 wherein the procedure light has a controllable iris to control the size of the beam of light from the procedure light.

8. The infant warming apparatus as defined in claim 1 wherein the overhead housing further contain a radiant heater to direct infrared radiation toward the infant platform.

9. The infant warming apparatus as defined in claim 1 wherein the infant apparatus includes an electrical controller mounted to said control handle to control the power to the procedure light.

10. The infant warming apparatus as defined in claim 1 wherein the procedure light produces a beam of light having a predetermined wavelength that provides phototherapy to an infant.

11. The infant warming apparatus as defined in claim 1 wherein the procedure light includes a filter to produce a beam of light of a particular color.

12. An infant warming apparatus, said infant warming apparatus comprising a base having an infant platform on which an infant is adapted to be positioned, an overhead housing located in a fixed position above the infant platform, a procedure light movably recessed within the overhead housing and positioned so as to direct a beam of light toward the infant platform, a control handle having a distal end extending downwardly from the procedure light so as to be accessible to a person to move the procedure light with respect to the fixed overhead housing to adjust the direction of the beam of light omnidirectionally, and an electrical controller located on said control handle to control the electrical power to the procedure light.

13. An infant warming apparatus as defined in claim 12 wherein the electrical controller is located at said distal end of said control handle.

14. An infant warming apparatus as defined in claim 12 wherein the procedure light further includes a lens holder that contains a lens, and wherein the lens holder is manually movable with respect to the lower housing to focus the beam of light directed from the procedure light toward the infant platform.

15. An infant warming apparatus as defined in claim 12 wherein the procedure light further includes a controllable iris to control the size of the beam of light directed from the procedure light toward the infant platform.

16. A method of directing a beam of light onto an infant platform of an infant warming apparatus, said method comprising the steps of:
> providing an infant warming apparatus having an overhead housing that is fixed in position with respect to the infant platform;
> providing a procedure light mounted for omnidirectional movement in a recessed, integrated location within the overhead housing with a control handle extending downward from the procedure light, said procedure light emanating a beam of light,
> controlling the direction of the beam of light emanating from the procedure light by manually manipulating the control handle to move the procedure light omnidirectionally with respect to the overhead housing to direct the light beam to a desired location on the infant platform.

17. A method as defined in claim 16 wherein the step of providing a procedure light includes the step of providing a procedure light having a variable lens and further including the step of manually adjusting the lens to focus the beam of light from the procedure light.

18. A method as defined in claim 16 wherein the step of providing a procedure light includes the step of providing a procedure light having an electrical controller located on the control handle.

19. A method as defined in claim 16 wherein the step of providing a procedure light comprises providing a procedure light having a controllable iris to vary the size of the beam of light emanating therefrom.

20. A method as defined in claim 16 wherein the step of providing a procedure light comprises providing a procedure light wherein the beam of light emanating therefrom is of a predetermined wavelength to provide phototherapy to an infant.

* * * * *